United States Patent
Peake et al.

(10) Patent No.: US 6,391,258 B1
(45) Date of Patent: May 21, 2002

(54) PRESSURE VESSEL HAVING ELECTROMECHANICAL LATCHING MECHANISM

(75) Inventors: Steven C. Peake; Jason A. Harms, both of Dubuque, IA (US)

(73) Assignee: Barnstead/Thermolyne Corporation, Dubuque, IA (US)

( * ) Notice: Subject to any disclaimer, the term of this patent is extended or adjusted under 35 U.S.C. 154(b) by 0 days.

(21) Appl. No.: 09/413,927

(22) Filed: Oct. 7, 1999

(51) Int. Cl.$^7$ .............................. A61L 2/08; A61L 2/00; E05F 15/00; E05C 1/06
(52) U.S. Cl. ........................... 422/26; 422/28; 422/33; 422/118; 422/295; 49/139; 49/380; 49/395; 49/476.1; 292/36; 292/145; 292/201; 292/279; 292/307
(58) Field of Search ................................ 422/1, 26, 33, 422/118, 292, 295, 108, 120; 292/36, 145, 201, 279, 307; 49/139, 380, 395, 476.1; 109/10, 17, 48, 52, 59 R, 70, 74

(56) References Cited

U.S. PATENT DOCUMENTS

| | | | | |
|---|---|---|---|---|
| 3,351,422 A | * | 11/1967 | Jones et al. | 21/94 |
| 3,385,655 A | * | 5/1968 | Huston et al. | 21/91 |
| 4,147,264 A | * | 4/1979 | Harvey et al. | 414/411 |
| 4,543,748 A | * | 10/1985 | North, Jr. | 49/395 |
| 4,745,708 A | * | 5/1988 | Roche | 49/395 |
| 4,891,910 A | * | 1/1990 | Cook et al. | 49/395 |
| 4,932,160 A | * | 6/1990 | Sperko | 49/254 |
| 5,040,332 A | * | 8/1991 | Aquilina | 49/200 |
| 5,223,229 A | * | 6/1993 | Brucker | 422/116 |
| 5,313,738 A | | 5/1994 | Thakur et al. | 49/394 |
| 5,792,427 A | * | 8/1998 | Hugh et al. | 422/109 |

* cited by examiner

*Primary Examiner*—Robert J. Warden, Sr.
*Assistant Examiner*—Monzer R. Chorbaji
(74) *Attorney, Agent, or Firm*—Wood, Herron & Evans, L.L.P.

(57) ABSTRACT

A pressure vessel, such as a bench top sterilizer, including a pressurizable chamber housing having an interior for receiving items to be sterilized. The chamber housing includes an access opening and the sterilizer or pressure vessel includes a door with hinge structure facilitating door movement between an opened condition, a latch condition and a latched and sealed condition. A seal is connected with at least one of the chamber housing and the door and is disposed in sealing engagement around the access opening when the door is in the latched and sealed condition. After latch structure on the door is initially actuated by a user, a motorized drive mechanism with a rotatable output connects with the latch structure such that rotation of the output moves the door from the initially latched condition to the latched and sealed condition.

28 Claims, 4 Drawing Sheets

PRESSURE VESSEL HAVING ELECTROMECHANICAL LATCHING MECHANISM

FIELD OF THE INVENTION

The present invention generally relates to pressure vessels and, more specifically, to latch mechanisms adapted to seal the door of a pressure vessel, such as a sterilizer used in scientific applications and other medical applications.

BACKGROUND OF THE INVENTION

Sterilizers and similar pressurized vessels typically include an outer housing which contains a chamber. The chamber has an access opening through which items are placed for sterilization within the chamber interior. Various apparatus and controls are provided for exposing the items within the chamber to sterilants under sterilizing conditions, often at elevated and/or reduced pressures. For example, during a typical sterilizing cycle, the chamber may experience portions of the cycle at elevated pressures and other portions of the cycle at reduced or vacuum pressures. A door is attached to the housing and is configured to cover the access opening. The door effects a pressure seal using a resilient gasket forming an interface between the door and the area of the chamber surrounding the access opening. Mechanical or pneumatic devices have been used to either expand or compress the gasket to effectively seal the access opening. Compression gaskets, as the name implies, operate under compression to seal the access opening, while other flexible pressure sealing gaskets are held in a sealing position by internal positive pressure within the chamber.

One problem with compression gaskets is that the user must either manually apply a large amount of force to close the latch of the door or tediously rotate a manual screw mechanism to obtain the required compression force against the seal. Furthermore, with the manual screw closure, there is a risk of over-tightening or under-tightening which, respectively, may reduce gasket life or result in leaks around the seal. A problem with flexible, positive pressure sealing gaskets is that, although these are simple and effortless to close, they may not be used in sterilizers that employ initial vacuum pulsing or final vacuum drying since they only seal with a positive internal pressure in the chamber. Another current design has the ability to open the door slightly after exposure to allow for improved convection in the chamber to enhance drying. This feature is used in sterilizers that do not employ a vacuum cycle within the chamber. These configurations are manually latched and sealed and use a solenoid to disengage the latch.

In view of various problems in the art, including those mentioned above, it would be desirable to provide a latch and closing mechanism for a pressure vessel that may be used under both positive and vacuum pressures, while also ensuring consistent seal compression during every use, even after seal wear.

SUMMARY OF THE INVENTION

To achieve these and other advantages, the present invention provides a pressure vessel especially useful in sterilizing procedures and including a pressurizable chamber housing having an interior for receiving items to be sterilized and further having an access opening to the chamber. Hinge structure connects a door to the chamber housing. The hinge structure facilitates movement of the door between an open condition, a latched condition and a latched and sealed condition with respect to the access opening. The door further includes latch structure for facilitating the latched condition. A seal is connected to at least one of the chamber housing and the door and is disposed in sealing engagement around the access opening when the door is in the latched and sealed condition. Finally, a powered drive mechanism with a movable output is mounted for operative connection with the latch structure or another part of the door such that powered movement of the output moves the door from the initially latched condition to the latched and sealed condition. The powered drive mechanism uses an actuator, such as a motor or a linear drive device. In another general aspect, a sensor is used to stop the actuator at a consistent seal compression level. The sensor may take on many different forms as those of ordinary skill will recognize and may comprise one sensing component or multiple components acting together as a sensor for this purpose.

As a more specific feature of the preferred embodiment, the drive mechanism includes a motor with a rotatable output. A motor control and sensor are coupled with the motor to sense an amount of compression being applied by the motorized drive mechanism to the seal. At a predetermined compression level, the motor control deactivates the motor. As illustrative examples, the motor may be a DC gear motor or other automatic drive device for supplying a linear actuation and the sensor may be an electric current sensor of many different possible designs. In a configuration utilizing a DC motor, a variance in the torque of the motor output will correspond directly with a variance in the electric current drawn by the motor. This is used as the preferred manner of detecting and controlling the amount of compression being applied to the seal since the motor may be operated by the motor control consistently to reach the same torque level and, therefore, the same seal compression level. Therefore, the seal will not be over-tightened or under-tightened. Another main advantage of this system is that seal wear will automatically be compensated for by the motor control and sensor due to the fact that the door is not closed to a fixed position, but rather to a fixed compression or motor torque.

In the preferred embodiment, the motorized drive mechanism further comprises a yoke connected with the rotatable motor output such that rotation of the output translates or, in other words, generally moves the yoke in a linear manner. Other closing mechanisms may be incorporated in the mechanical design as well. These might include cam mechanisms, rotary mechanisms and other mechanical systems that may, for example, rely on vacuum pressure in the chamber to at least assist in obtaining a sealed condition. The yoke is further adapted to be connected with the latch structure of the door in the latched condition such that translation of the yoke by the rotatable output moves the door to the latched and sealed condition. As one example, the motor output may include a threaded shaft and the yoke may include an internally threaded hole for receiving the threaded shaft. The latch structure may further comprise a movable handle and at least one engagement member connected for movement by the handle between latched and unlatched conditions. The engagement member is adapted to connect with the motorized drive mechanism in the latched condition and, more specifically, to the yoke via a pair of pins.

As another feature of the invention, a stop member is provided to prevent unlatching in the latched and sealed condition. This feature may be used to advantage in manual latch and seal configurations as well as the automatic or powered system as generally described herein. The engagement member includes a stop member configured to prevent movement of the engagement member to the unlatched condition when the door is in the latched and sealed condition. Since the pins will be frictionally engaged in holes contained in the yoke when latched, this frictional engagement will also help prevent unlatching, especially when the interior of the chamber housing is under positive pressure.

Since the door is closed with the use of a motorized screw shaft or other comparable element, it cannot be opened until the screw shaft is rotated to disengage the door. This provides the ability to lock the door with electrical motor controls to fully meet sterilization standards. The user will not be able to open the door until the sterilization cycle has completed and the motor, such as a gear motor, operates to release the latch structure.

These and other features, advantages and objectives of the invention will become more readily apparent to those of ordinary skill in the art upon review of the following detailed description of the preferred embodiment, taken in conjunction with the accompanying drawings.

DETAILED DESCRIPTION OF THE PREFERRED EMBODIMENT

Figure 1:
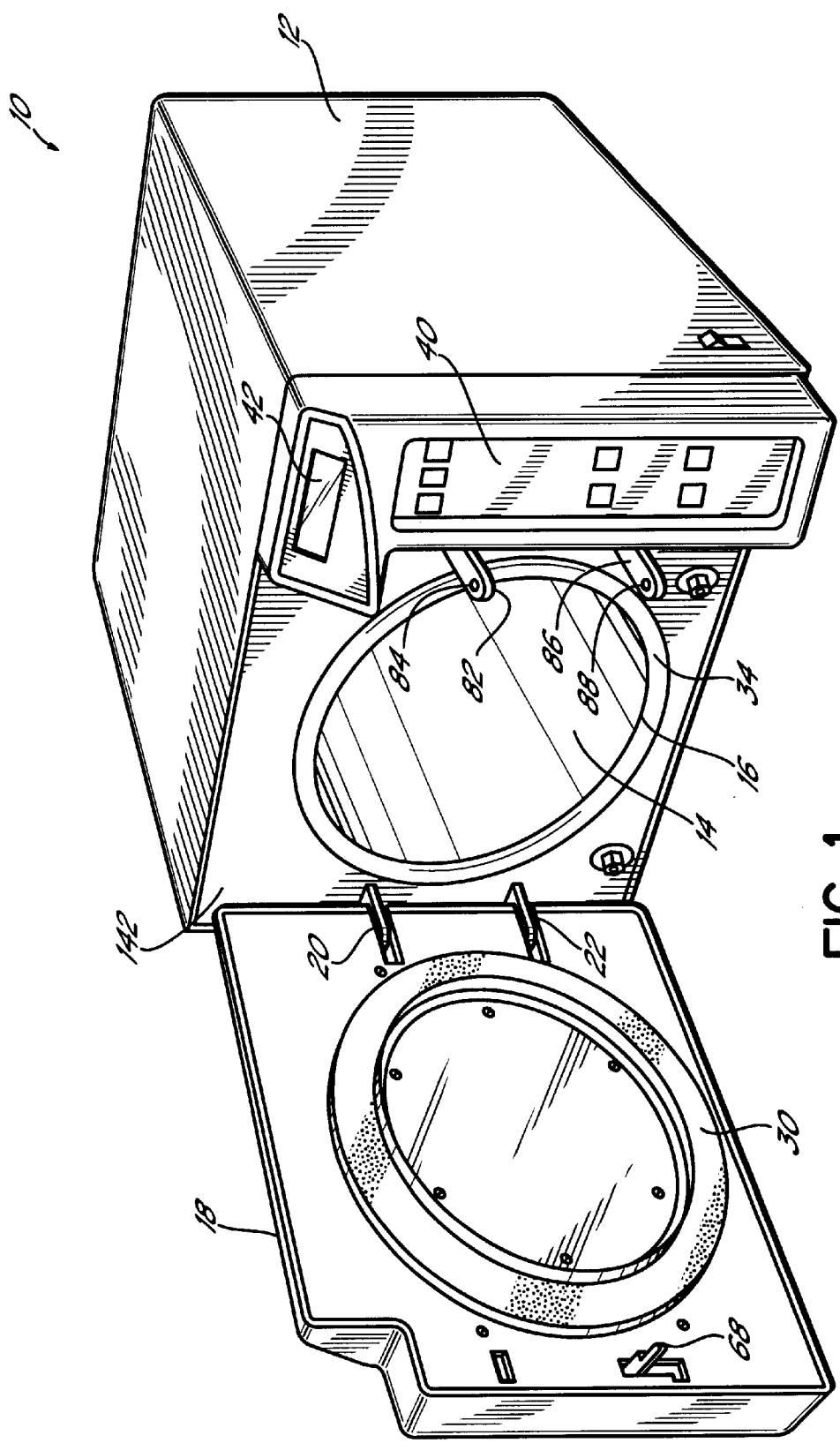
FIG. 1 is a perspective view of a bench top sterilizer incorporating a latch mechanism constructed according to a preferred embodiment of the invention.

Referring first to FIG. 1, the preferred embodiment of the invention is illustrated with respect to a bench top sterilizer 10 of the type typically used in scientific applications and other medical or dental applications requiring sterilization of selected items. The specifics of the sterilization components and control system for carrying out specific sterilization cycles are not shown or described as these do not specifically relate to the present invention. However, sterilizer 10 may be of the type sold by Barnstead/Thermolyne Corporation as a Sterile PV unit. It will be appreciated that the features of the present invention may be incorporated into various types of pressure vessels, including other types of sterilizers.

Sterilizer 10 more specifically comprises a pressurizable chamber housing 12 having an interior 14 for receiving items to be sterilized. Interior 14 is accessed through an opening 16 when a door 18 is opened by a user. Door 18 includes hinge structure 20, 22 along one side thereof and further includes a seal 30 for surrounding access opening 16 in the sealed condition. Optionally, seal 30 may be connected to chamber housing 12 in surrounding relation to access opening 16 or a pair of sealing gaskets might be used that interface to create a seal when door 18 is closed and sealed, as further discussed below. In the preferred embodiment, seal 30 engages a sealing surface 34 disposed around the periphery of access opening 16. Sterilizer 10 further includes a control panel 40 and a display 42 as is generally conventional.

Figure 2:
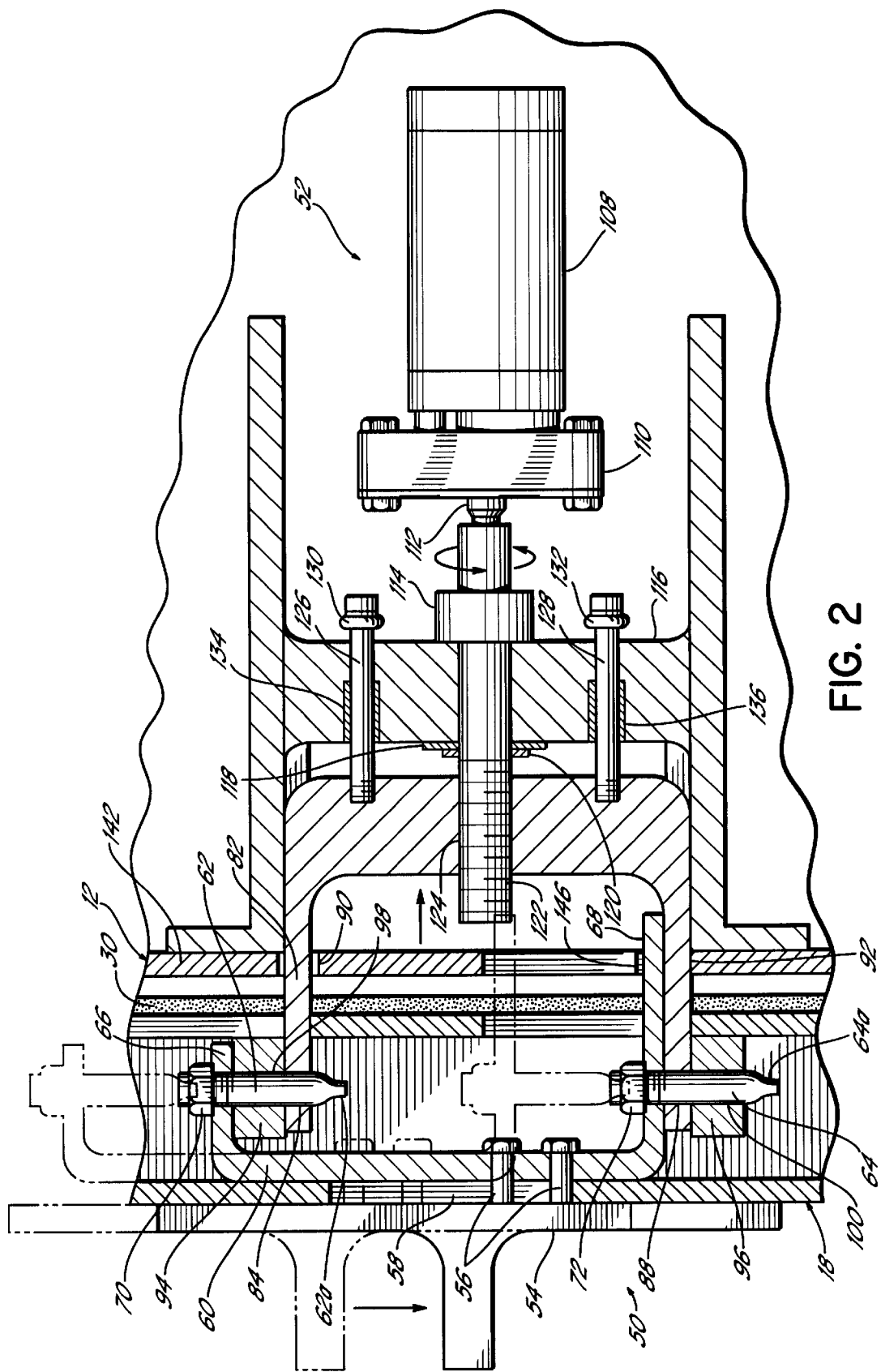
FIG. 2 is a cross sectional view taken along line 2—2 of FIG. 1 and showing the door of the sterilizer in a latched condition.

Referring now to FIG. 2, door 18 further includes a latch structure 50 operatively connected to a motorized drive mechanism 52. In the preferred embodiment, latch structure 50 includes a handle 54 connected by a pair of horizontal pins 56, for example, which extend through a slot 58 within door 18 and are rigidly affixed to a C-shaped bracket 60. Other handle configurations may be used as well. C-shaped bracket 60 includes a pair of vertical pins 62, 64 spaced apart and connected rigidly with respective upper and lower arms 66, 68 of bracket 60 by nuts 70, 72. A C-shaped yoke 80 forms part of motorized drive mechanism 52, as further discussed below, and includes an upper arm 82 with a hole 84 and a lower arm 86 with a hole 88. Arms 82, 86 extend through respective apertures 90, 92 in chamber housing 12. A pair of rigid frame members 94, 96 are secured within door 18 and also include respective holes 98, 100. When door 18 is in the latched condition shown in FIG. 2, upper and lower vertical pins 62, 64 align with respective holes 84, 98 and 88, 100. When handle 54 is lifted, as shown in dash-dot lines, this allows door 18 to be closed to the condition shown in FIG. 2, such that pins 62, 64 align and may drop into holes 84, 98 and 88, 100. In the preferred embodiment, seal 30 engages housing 12 on the hinge side to provide stopping resistance at a location appropriate to allow pins 62, 64 to drop into holes 84, 98 and 88, 100. Other stops may be provided for allowing this locating function as well. Pins 62, 64 have tapered ends 62a, 64a to provide a margin of error of about ±⅛" for obtaining the necessary initial latching position of door 18.

Motorized drive mechanism 52 includes a motor, which is preferably a DC gear motor, connected with a bracket 110 to the interior of chamber housing 12. Motor 108 includes a rotatable output shaft 112 extending through a thrust bearing 114, which bears against a rigid support member 116 connected within chamber housing 12, and a washer 118 held on the opposite side thereof by a clip 120. An outer end of output shaft 112 includes external threads 122 that mate with internal threads 124 contained in one end of yoke 80. A pair of guide pins 126, 128 are also threaded into yoke 80 and include respective stops 130, 132 for preventing excessive outward extension of yoke 80. Guide pins 126, 128 slide within respective bushings 134, 136.

Figure 3:
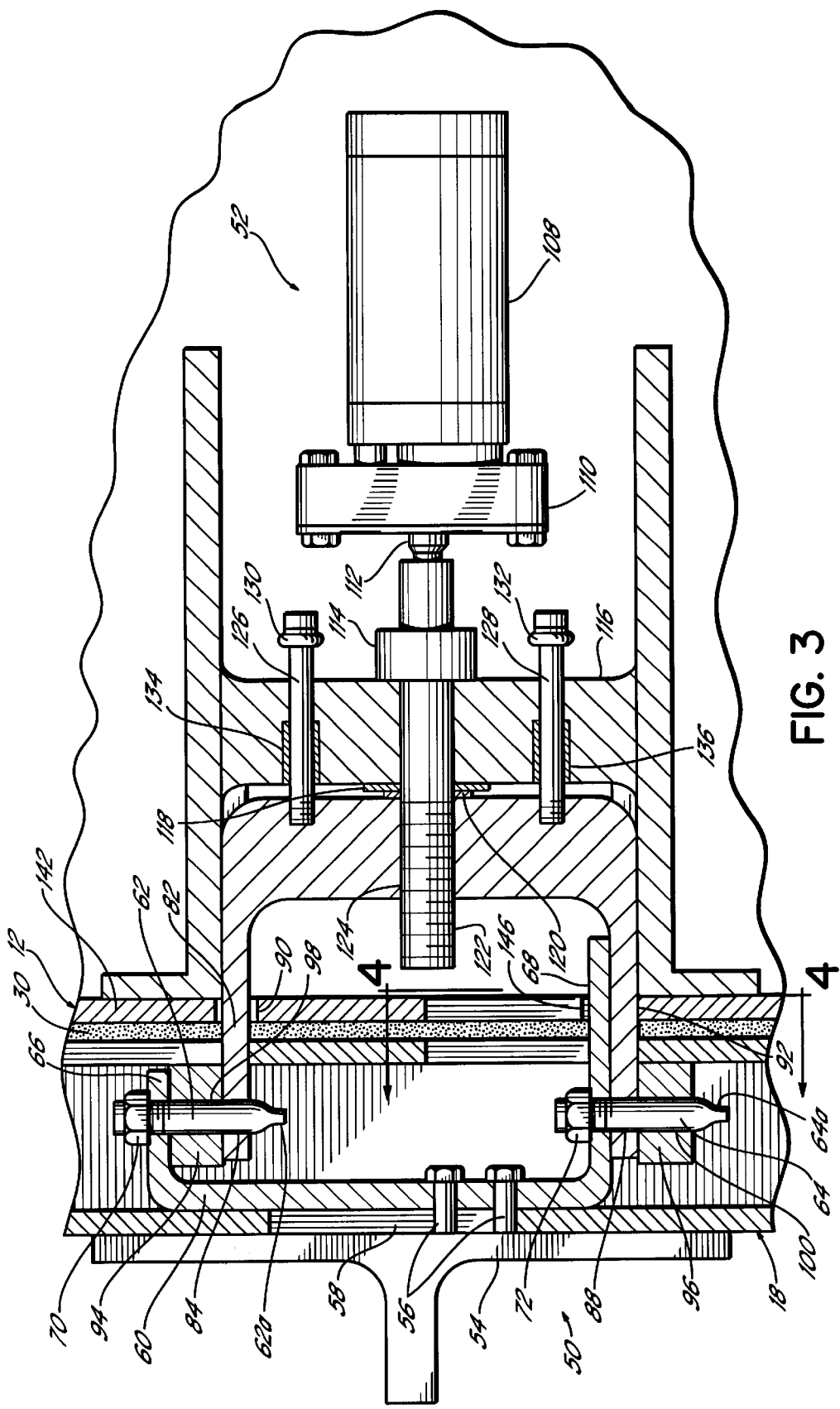
FIG. 3 is a cross sectional view similar to FIG. 2, but showing the door in a latched and sealed condition.

As illustrated in FIG. 3, which shows the latched and sealed condition of door 18, it will be appreciated that output shaft 112 of motor 108 has rotated so that the interaction of threads 122 and 124 causes yoke 80 to move to the right. This pulls seal 30 against sealing surface 34. When motor 108 is stopped, door 18 is effectively locked and cannot be opened without reactuation of motor 108 in the opposite direction. Positive pressure within interior 14 may contribute to a user's inability to raise handle 54 while door 18 is in the latched and sealed condition shown in FIG. 3 due to the increase in friction of pins 62, 64 against upper and lower arms 82, 86 and rigid frame members 94, 96. In the preferred embodiment, this condition exists only when interior 14 is under positive pressure. Depending on the design of the sterilizer, this condition may exist under positive or negative pressure.

Figure 4:
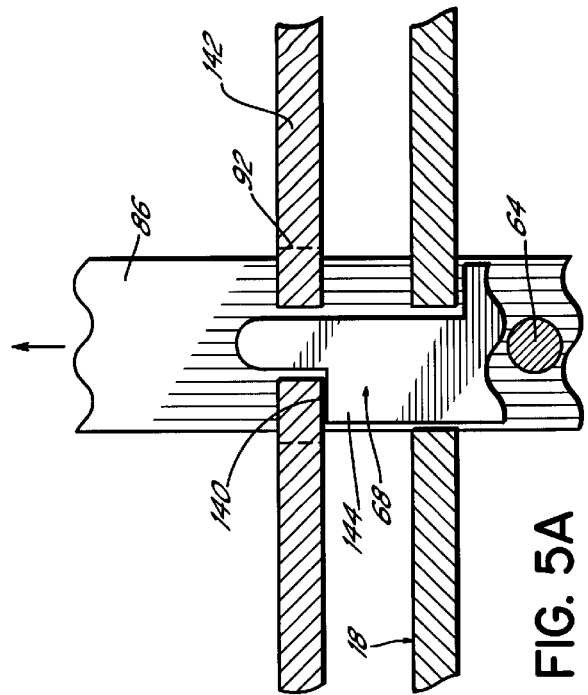
FIG. 4 is a fragmented plan view of a portion of the latch mechanism taken along line 4—4 of FIG. 3.
Figure 5A:
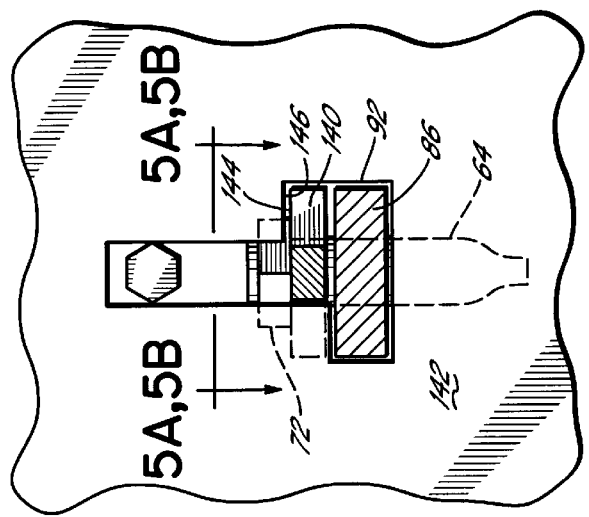
FIG. 5A is a cross sectional view taken along line 5—5 of FIG. 4 and showing the door in the latched condition.
Figure 5B:
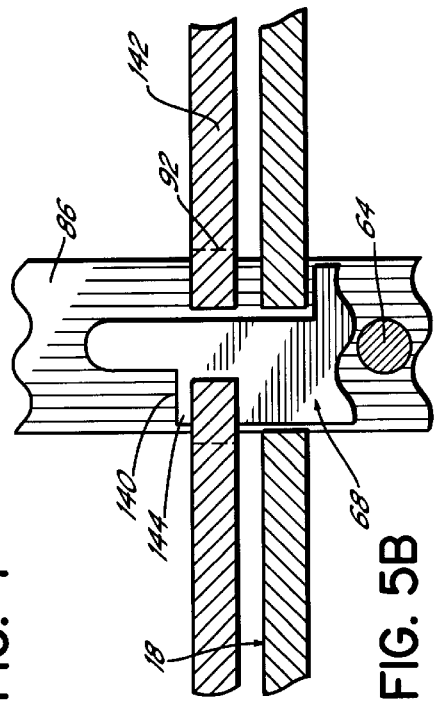
FIG. 5B is a cross sectional view similar to FIG. 5, but showing the door in a latched and sealed condition.

Referring now to FIGS. 4, 5A and 5B, a further handle locking feature is provided to ensure that handle 54 (FIG. 2) may not be lifted when door 18 is in the locked and sealed condition, as shown in FIGS. 3 and 5B. Specifically, arm 68 of C-shaped bracket 60 includes an inset portion 140 normally disposed outside of an outer metal skin 142 forming part of chamber housing 12, as shown best in FIG. 5A. Thus, in this position, latch structure 50 and, specifically, handle 54 may freely move between latched and unlatched conditions. In the preferred embodiment, this is especially true when interior 14 is under vacuum. However, when motor 108 is activated to pull yoke 80 and, therefore, door 18 to the sealed condition shown in FIG. 3, lower arm 68 of bracket 60 will be pulled further into aperture 92 such that a wider portion 144 is disposed beneath edge 146 of aperture 92 as shown in FIG. 5B. This physically prevents upward movement of handle 54 and, therefore, prevents unlatching of latch structure 50 until motor 108 is actuated sufficiently in a reverse direction.

Figure 6:
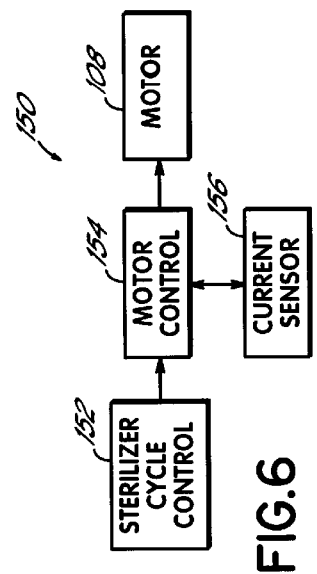
FIG. 6 is a block diagram schematically illustrating a control system associated with the sterilizer.

A schematic block diagram of a control system 150 for sterilizer 10 is shown in FIG. 6. System 150 may be conventional in most respects, such as by including a generally conventional sterilizer cycle control 152. In accordance with the invention, motor 108 includes a motor control 154 which is connected with or integrated with a current sensor 156. In the preferred embodiment, and as mentioned above, motor 108 is a DC gear motor including an integrated motor control and current sensor. When activated by sterilizer cycle control 152 after latching as shown in FIG. 2, motor control 154 activates motor 108 in order to draw door 18 to the position as shown in FIG. 3. At a predetermined torque level, determined by a corresponding electrical current level detected by sensor 156, motor control will be directed to deactivate motor 108. This will ensure that seal 30 contacts sealing surface 34 at a preselected torque level of motor 108 which may correspond to a desired compression level of seal 30 against sealing surface 34.

In the preferred embodiment, the desired torque level for achieving an effective seal is 50 in.-lbs. Many different manners of sensing the proper compression level may be chosen upon review of the present disclosure. In the preferred embodiment, and as one illustrative example, the electrical current drawn by motor 108 is measured through the use of a sense resistor, i.e., a very low ohm resistor. The voltage across the sense resistor is proportional to the current directed through the motor 108, which is consequently proportional to the torque of the motor shaft 112. This voltage is directed through an op-amp circuit to amplify the voltage at the sense resistor. The amplified sense voltage is then compared to a fixed voltage which is the threshold level of desired torque.

While the present invention has been illustrated by a description of the preferred embodiment and while this embodiment has been described in some detail, it is not the intention of the Applicant to restrict or in any way limit the scope of the appended claims to such detail. Additional advantages and modifications will readily appear to those skilled in the art. This has been a description of the present invention, along with the preferred methods of practicing the present invention as currently known. Various aspects of this invention may be used alone or in different combinations.

The scope of the invention itself should only be defined by the appended claims, wherein we claim:

1. A pressure vessel for use in sterilizing procedures, the pressure vessel comprising:
    a pressurizable chamber housing having an interior for receiving items to be sterilized and further having an access opening to said interior,
    a door positionable relative to said access opening among an open condition, a latched condition, and a latched and sealed condition,
    a latch structure connected with said door,
    a seal connected to at least one of said chamber housing and said door and disposed in sealing engagement around said access opening when said door is in the latched and sealed condition, and
    a powered drive mechanism connected with said chamber housing, said powered drive mechanism having an actuator with a movable output and a movable latch-receiving structure mounted to said movable output, said latch-receiving structure configured to releasably engage said latch structure to provide the latched condition of the door and said movable output operable to translate said latch-receiving structure and said latch structure when in the latched condition such that said door moves from the latched condition to the latched and sealed condition.

2. The pressure vessel of claim 1 further comprising:
    a control connected with said actuator, and
    a sensor operatively coupled with said control and operative to sense an amount of compression being applied by said actuator to said seal.

3. The pressure vessel of claim 2, wherein said actuator is an electric motor having a rotatable output and wherein electrical current drawn by said motor varies in a defined relation to a variance in torque at the output, and said sensor further comprises an electrical current sensor.

4. The pressure vessel of claim 3, wherein said control operates to deactivate said motor when said sensor detects a predetermined electrical current level drawn by said motor.

5. The pressure vessel of claim 1, wherein said latch-receiving structure further comprises:
    a yoke mounted to the movable output, said yoke translated by powered movement of said output for moving said door to the latched and sealed condition.

6. The pressure vessel of claim 1, wherein said latch structure further comprises:
    a movable handle, and
    at least one engagement member connected for movement by said handle between the latched condition and the unlatched condition, said engagement member adapted to connect with said latch-receiving structure in the latched condition.

7. The pressure vessel of claim 6, wherein said engagement member further comprises a stop member configured to prevent movement of said engagement member to the unlatched condition when said door is in the latched and sealed condition.

8. The pressure vessel of claim 6, wherein said engagement member further comprises a pair of pins adapted to be connected to said latch-receiving structure when in the latched condition.

9. The pressure vessel of claim 8, wherein said engagement member further comprises a bracket including a stop member configured to prevent movement of said engagement member to the unlatched condition when said door is in the latched and sealed condition.

10. A pressure vessel for use in sterilizing procedures, the pressure vessel comprising:
    a pressurizable chamber housing having an interior for receiving items to be sterilized and further having an access opening to said interior,
    a door positionable relative to said access opening among an open condition, a latched condition, and a latched and sealed condition,
    a latch structure connected with said door, said latch structure including a plurality of spaced-apart pins,
    a seal connected to at least one of said chamber housing and said door and disposed in sealing engagement around said access opening when said door is in the latched and sealed condition, a motorized drive mechanism connected with said chamber housing, said drive mechanism including a motor with a rotatable output and a movable yoke connected with said rotatable output, said yoke having a plurality of spaced-apart apertures positioned and configured to releasably engage respective ones of said plurality of pins to provide the unlatched condition of said door when disengaged and the latched condition of said door when engaged, and said yoke and said plurality of pins when in the latched condition being translated by rotation of said motorized drive mechanism such that said door moves from the latched condition to the latched and sealed condition.

11. The pressure vessel of claim 10, further comprising a movable handle operably connected with said latch structure for moving said plurality of pins between the latched condition and the unlatched condition.

12. The pressure vessel of claim 11, wherein said latch structure further comprises a stop member configured to prevent movement of said plurality of pins to the unlatched condition when said door is in the latched and sealed condition.

13. The pressure valve of claim 12, wherein said stop member is configured to extend into said chamber housing when said door is in the latched and sealed condition.

14. The pressure vessel of claim 13, wherein said latch structure further comprises a bracket including said stop member configured to prevent movement of said handle to the unlatched condition when said door is in the latched and sealed condition.

15. A pressure vessel for use in sterilizing procedures, the pressure vessel comprising:
   a pressurizable chamber housing having an interior for receiving items to be sterilized and further having an access opening to said interior,
   a door positionable relative to said access opening among an open condition, a latched condition, and a latched and sealed condition,
   a latch structure connected with said door,
   a handle coupled with said latch structure and normally movable between at least an unlatched condition and a latched condition corresponding to the latched condition of said door,
   a seal connected to at least one of said chamber housing and said door and disposed in sealing engagement around said access opening when said door is in the latched and sealed condition,
   a drive mechanism mounted for operative connection with said latch structure such that, when said door and said handle are in the latched condition, movement of said drive mechanism moves said door from the latched condition to the latched and sealed condition, and
   a stop member operatively connected with said latch structure and configured to prevent movement of said handle to the unlatched condition when said door is in the latched and sealed condition.

16. The pressure vessel of claim 15, wherein the drive mechanism further comprises:
   a powered actuator having a movable output configured to be coupled to said latch structure to move said door from the latched condition to the latched and sealed condition,
   a control connected with said actuator, and
   a sensor coupled with said control and operative to at least indirectly sense an amount of compression being applied to said seal.

17. The pressure vessel of claim 16, wherein said powered actuator is a motor in which electrical current drawn by said motor varies in a defined relation to a variance in torque at said output, and said sensor further comprises an electrical current sensor.

18. The pressure vessel of claim 17, wherein said control operates to deactivate said motor when said sensor detects a predetermined electrical current level drawn by said motor.

19. The pressure vessel of claim 16, wherein said drive mechanism further comprises:
   a movable yoke connected with said output such that movement of said output translates said yoke, said yoke further adapted to be connected with said latch structure in said latched condition such that translation of said yoke by said output moves said door to the latched and sealed condition.

20. The pressure vessel of claim 15, wherein said latch structure further comprises:
   a movable handle, and
   at least one engagement member connected for movement by said handle between the latched condition and the unlatched condition, said engagement member adapted to connect with said drive mechanism in the latched condition.

21. The pressure vessel of claim 20, wherein said stop member is connected for movement with said engagement member.

22. The pressure vessel of claim 20, wherein the engagement member further comprises a pair of pins adapted to be connected to said yoke when in the latched condition.

23. A method of sealing a pressure vessel comprising a chamber housing having an interior accessed through an opening in the housing, the pressure vessel having a door hingedly connected to the housing, said method comprising:
   providing a seal connected to one of the chamber housing and the door,
   providing the door with a latch structure,
   providing a power drive mechanism with a rotatable output,
   connecting the latch structure to the rotatable output of the power drive mechanism, and
   actuating the power drive mechanism to rotate the output and translate the latch structure to move the door from a latched condition to a latched and sealed condition in which the seal is compressed against a sealing surface.

24. The method of claim 23 further comprising sensing an amount of compression on said seal and in response thereto deactuating the power drive mechanism.

25. A method of sealing a pressure vessel for use in sterilizing procedures, the pressure vessel comprising a housing having an interior accessed through an opening in the housing, the pressure vessel having a door hingedly connected to the housing to enable the door to move among an open condition, a latched condition, and a latched and sealed condition, the method comprising:
   providing a seal connected to one of the chamber housing and the door,
   providing a power drive mechanism with a movable output,
   providing the door with a latch structure,
   operatively connecting the latch structure to the power drive mechanism, and
   actuating said power drive mechanism to move the output and translate the latch structure, thus moving the door from the latched condition to the latched and sealed condition.

26. The method of claim 25 further comprising sensing an amount of compression on the seal and in response thereto deactuating the power drive mechanism.

27. The method of claim 25 wherein operatively connecting the latch structure to the power drive mechanism comprises passing a pair of pins through holes in a C-shaped yoke.

28. The method of claim 25 wherein actuating said power drive mechanism comprises supplying current to a motor.

* * * * *

UNITED STATES PATENT AND TRADEMARK OFFICE
CERTIFICATE OF CORRECTION

PATENT NO. : 6,391,258 B1
DATED : May 21, 2002
INVENTOR(S) : Peake et al.

It is certified that error appears in the above-identified patent and that said Letters Patent is hereby corrected as shown below:

<u>Title page,</u>
Item [57], ABSTRACT reads "a latch condition" and should read -- a latched condition --.

<u>Column 5,</u>
Line 48, reads "Applicant" should read -- Applicants --.

<u>Column 7,</u>
Line 22, reads "The pressure valve" and should read -- The pressure vessel --.

Signed and Sealed this

Eleventh Day of February, 2003

JAMES E. ROGAN
*Director of the United States Patent and Trademark Office*